(12) United States Patent
Dowling

(10) Patent No.: US 7,318,889 B2
(45) Date of Patent: Jan. 15, 2008

(54) APPARATUS, SYSTEM AND METHOD FOR EXTENDING THE LIFE OF SACRIFICIAL ANODES ON CATHODIC PROTECTION SYSTEMS

(75) Inventor: David B. Dowling, New York, NY (US)

(73) Assignee: Applied Semiconductor International, Ltd., Neuenhof (CH)

( * ) Notice: Subject to any disclaimer, the term of this patent is extended or adjusted under 35 U.S.C. 154(b) by 101 days.

(21) Appl. No.: 11/142,492

(22) Filed: Jun. 2, 2005

(65) Prior Publication Data

US 2007/0023295 A1    Feb. 1, 2007

(51) Int. Cl.
*C23F 13/04* (2006.01)

(52) U.S. Cl. .............. 205/725; 205/724; 205/730; 205/731; 205/734; 205/735; 205/736; 205/740; 204/196.02; 204/196.04; 204/196.06; 204/196.07; 204/196.11; 204/196.12; 204/196.16; 204/196.26; 204/196.37

(58) Field of Classification Search .............. 205/725, 205/724, 730, 731, 734, 735, 736, 740; 204/196.02, 204/196.04, 196.06, 196.07, 196.11, 196.12
See application file for complete search history.

(56) References Cited

U.S. PATENT DOCUMENTS

| | | | |
|---|---|---|---|
| 5,009,757 A | 4/1991 | Riffe et al. | |
| 5,055,165 A | 10/1991 | Riffe et al. | |
| 5,346,598 A | 9/1994 | Riffe et al. | |
| 5,352,342 A | 10/1994 | Riffe | |
| 5,478,451 A | 12/1995 | Riffe | |
| 5,643,424 A | 7/1997 | Riffe et al. | |
| 6,325,915 B1 | 12/2001 | Dowling et al. | |
| 6,524,466 B1 | 2/2003 | Bonaventura et al. | |
| 6,551,491 B2 | 4/2003 | Dowling et al. | |
| 6,562,201 B2 | 5/2003 | Dowling | |
| 6,811,681 B2 * | 11/2004 | Dowling et al. | ............ 205/725 |
| 6,890,420 B2 | 5/2005 | Dowling | |
| 7,029,569 B2 * | 4/2006 | Dowling et al. | ............ 205/725 |
| 2005/0109635 A1 | 5/2005 | Dowling et al. | |

* cited by examiner

*Primary Examiner*—Bruce F. Bell
(74) *Attorney, Agent, or Firm*—Oblon, Spivak, McClelland, Maier & Neustadt, P.C.

(57) ABSTRACT

An apparatus, system, method and computer program product directed to controlling corrosion of a conductive structure in contact with a corrosive environment and electrically connected to one or more anodes, wherein the anodes are less noble than the conductive structure, where the corrosion is controlled by a controllable filter and a corresponding electronic control unit configured to process at least one stored or measured parameter, and wherein the apparatus, system and method serve to prolong the lifetime of the one or more anodes by reducing, minimizing or substantially eliminating their sacrificial character.

47 Claims, 8 Drawing Sheets

APPARATUS, SYSTEM AND METHOD FOR EXTENDING THE LIFE OF SACRIFICIAL ANODES ON CATHODIC PROTECTION SYSTEMS

BACKGROUND OF THE INVENTION

1. Field of the Invention

The present invention relates to an apparatus, system, and method for extending the lifetime of a sacrificial anode that is part of a cathodic protection based anti-corrosion system.

2. Discussion of the Background Art

The annual cost of metallic corrosion in the United States economy is approximately $300 billion, according to a report released by Battelle and the Specialty Steel Industry of North America entitled "Economic Effects of Metallic Corrosion in the United States," dated 1995, the entire contents of which is hereby incorporated by reference. The report estimates that about one-third of the cost of corrosion ($100 billion) is avoidable and could be saved by broader application of corrosion-resistant materials and application of best anti-corrosive practice from design through maintenance. The estimates result from a partial update by Battelle scientists of the findings of a study conducted by Battelle and the National Institute of Standards and Technology titled "Economic Effects of Metallic Corrosion in the United States," the entire contents of which are hereby incorporated by reference. The original work in 1978 included an estimate that, in 1975, metallic corrosion cost the U.S. $82 billion (4.9 percent of the Gross National Product), and approximately $33 billion was avoidable because best practices were not used at the time.

A variety of methods for controlling corrosion have evolved over the past several centuries, with particular emphasis on methods to extend the life of metallic structures in corrosive environments. These methods typically include (a) cathodic protection based systems, which use anodes made from a metal that is less noble that the metal substrate that is being protected, so that it is the anode that sacrificially corrodes rather than the substrate to which it is connected, and (b) protective coatings, which are used principally to upgrade the corrosion resistance of ferrous metals, such as steel, and some nonferrous metals, such as aluminum, and to avoid the necessity for using more costly alloys. Thus, they both improve performance and reduce costs. However, such protective coatings typically have several pitfalls, including poor applicability to non-metallic structures that suffer from corrosion or fouling.

Protective coatings fall into two main categories. The largest of these categories is the topical coating such as a paint that acts as a physical barrier against the environment. The second category consists of sacrificial coatings, such as zinc or cadmium that are designed to preferentially corrode in order to save the base metal from attack.

Cathodic protection and coatings are both engineering disciplines with a primary purpose of mitigating and preventing corrosion. Each process is different: cathodic protection prevents corrosion by introducing an electrical current from external sources (such as a sacrificial anode) to counteract the normal electrical chemical corrosion reactions whereas coatings form a barrier to prevent the flow of corrosion current or electrons between the naturally occurring anodes and cathodes or within galvanic couples. Each of these processes provided limited success. Coatings by far represent the most wide-spread method of general corrosion prevention (see Leon et al U.S. Pat. No. 3,562,124 and Hayashi et al U.S. Pat. No. 4,219,358). Cathodic protection, however, has been used to protect hundreds of thousands of miles of pipe and acres of steel surfaces subject to buried or immersion conditions.

Cathodic protection is used to reduce the corrosion of the metal surface by providing it with enough cathodic current to make its anodic dissolution rate become negligible (for examples, see Pryor, U.S. Pat. No. 3,574,801; Wasson U.S. Pat. No. 3,864,234; Maes U.S. Pat. No. 4,381,981; Wilson et al U.S. Pat. No. 4,836,768; Webster U.S. Pat. No. 4,863,578; and Stewart et al U.S. Pat. No. 4,957,612). Cathodic protection operates by extinguishing the potential difference between the local anodic and cathodic surfaces through the application of sufficient current to polarize the cathodes to the potential of the anodes. In other words, the effect of applying cathodic currents is to reduce the area that continues to act as an anode, rather than reduce the rate of corrosion of such remaining anodes. Complete protection is achieved when all of the anodes have been extinguished. From an electrochemical standpoint, this indicates that sufficient electrons have been supplied to the metal to be protected, so that any tendency for the metal to ionize or go into solution has been neutralized.

Recent work in the study of corrosion has found that electrochemical corrosion processes appear to be associated with random fluctuations in the electrical properties of electrochemical systems, such as cell current and electrode potential. These random fluctuations are known in the art as "noise." About 20 years ago, scientists found that all conductive materials begin corroding as soon as they are produced due to electrochemical activity caused by impurities in the material. It was later found that this activity could be monitored using electronic instruments detecting the current generated, now commonly referred to as "corrosion noise." Essentially, the greater the magnitude of this current, the "noisier" the material and the faster the rate of corrosion. For example, steel is "noisier" than bronze and corrodes at a faster rate. Researchers have begun to apply noise analysis techniques to study the processes of corrosion in electrochemical systems.

FIG. 1 is a representation of electrochemical noise present in untreated metal 101. The randomly fluctuating voltage is measured and displayed as waveform 102 (shown as a sawtooth waveform, but an actual waveform would have broader band components and would be stochastic in nature).

FIG. 2 is a graph of corrosion potential versus time with various filters. The horizontal axis 401 measures time in days while the vertical axis 402 represents potential relative to the semiconductor element measured in milli-volts. During an experiment directed to determining optimum filter characteristics for various corrosion environments, measurements were taken for seven systems at three points in time. The measured potential for each of seven filter configurations were recorded for those three samples and are indicated by various symbols listed in the legend. The graph displays the various results for each of the seven filters at the sampling points indicated from 410 through 430.

One solution to corrosion problems has been proposed in the semiconductor coatings and related systems of Dowling's U.S. Pat. No. 6,325,915, U.S. Pat. No. 6,402,933, U.S. Pat. No. 6,562,201 and the Electronic Control Unit (ECU) of U.S. Pat. No. 6,811,681, the entire contents of each being hereby incorporated by reference. The semiconductive coating, ECU and system of the Dowling patents can be used with a variety of conductive substrates to provide an array of interesting properties.

SUMMARY OF THE INVENTION

Accordingly, one object of the present invention is to provide a method for prolonging the life of sacrificial anodes in conventional cathodic protection systems.

Another object of the invention is to provide an apparatus and system for prolonging the life of sacrificial anodes of cathodic protection systems.

Another object of the invention is to provide an improved cathodic protection system, having an Electronic Control Unit (ECU), a controllable filter (optionally including a fixed, passive filter), a substrate, and one or more anodes comprising a metal or metal alloy that is less noble than the substrate.

These and other objects of the present invention, either individually or in combinations thereof, are achieved by the inventive system and method described herein. The present inventor recognized that an Electronic Control Unit (ECU) and controllable filter, such as described in U.S. Pat. No. 6,811,681 (hereby incorporated by reference), can be used to extend the lifetime of sacrificial anodes in an otherwise conventional cathodic protection system, by electrically connecting the ECU to either the substrate being protected (the cathode) or to the sacrificial anode. These benefits are achieved via a method for monitoring noise generated by the cathodic protection system and controlling a filter, that is optionally, although not limited to, using adjustable filter components and/or fixed components based on a set of predetermined and/or measured parameters in response to the corrosion noise generated in the system, thereby controlling (significantly reducing) the rate at which the sacrificial anode of the cathodic protection system is expended. The set of predetermined and/or measured parameters include at least one of: temperature, salinity/water purity, humidity, age, short term duty cycle, long term duty cycle, immediate speed of vessel, vessel speed history, immediate geographic location, geographic location history, age of coating, coating deterioration, thickness of coating, surface area coated, and shape of coated area.

The present invention is aimed at the prevention of corrosion in aviation structures/craft; automotive structures/vehicles; bridges; marine vessels/structures; pipelines; rail cars/structures; steel structures; and storage tanks, although may be used with other objects as well, so long as the structures are susceptible to protection with conventional cathodic protection systems.

As determined by the present inventor, a controllable filter and controller may be used in a corrosive noise reducing system where the controller dynamically adjusts the filter characteristics of the corrosive noise reducing system by taking into account various parameters so as to balance the system's anti-corrosion characteristics. A non-limiting list of examples of these parameters includes one or more of: temperature, salinity/water purity, humidity, age, short term duty cycle, long term duty cycle, anode duty cycle, immediate speed of vessel, vessel speed history, immediate geographic location, geographic location history, and shape/size of conductive substrate. In view of the discovery that it is possible to strike this balance between the system's anti-corrosion characteristics, particularly with respect to the sacrifice rate of the sacrificial anode of the cathodic protection system, the present inventor identified, and describes herein, systems, devices, algorithms, methods, and computer program products for controlling filter operations associated with an anti-corrosion sacrificial anode based cathodic protection system and a corrosive noise reducing system.

BRIEF DESCRIPTION OF THE FIGURES

A more complete appreciation of the invention and many of the attendant advantages thereof will be readily obtained as the same becomes better understood by reference to the following detailed description when considered in connection with the accompanying Figures, wherein.

DETAILED DESCRIPTION OF THE PREFERRED EMBODIMENTS

The present invention provides a cathodic protection system having an Electronic Control Unit (ECU), a controllable filter, a substrate cathode and one or more anodes wherein the ECU and controllable filter are electrically connected to either or both of the substrate cathode or the one or more anodes of the system.

The ECU of the present invention corresponds to that of U.S. Pat. No. 6,811,681, incorporated herein by reference. The one or more anodes of the present invention can be made of any conductive or semiconductive material, so long as the one or more anodes is electrically less noble than the conductive structure (the substrate cathode) being protected. Accordingly, the one or more anodes comprises at least one material selected from the group consisting of conductive organic polymers, metals, metal alloys and non-metal semiconductor materials, wherein said at least one material is less noble than said conductive structure. Preferred conductive organic polymers include, but are not limited to polyacetylenes, polyphenylenes, polyfurans, polythiophenes, polypyrroles, poly(arylene vinylenes), polyanilines, and doped compositions thereof. Preferred metals or metal alloys include, but are not limited to Zn, Ti, Al, Ga, Ce, Mg, Ba, Cs, the corresponding metal oxides and alloys thereof. Further, the metals or metal alloys can be a mixture of one or more metals and one or more metal oxides obtained therefrom. Preferred such mixtures are mixtures of at least one metal selected from the group consisting of Zn, Ti, Al, Ga, Ce, Mg, Ba and Cs, and one or more metal oxides obtained therefrom. In a most preferred case, the one or more anodes can be made of zinc, or a combination of zinc/zinc oxide.

Figure 1:
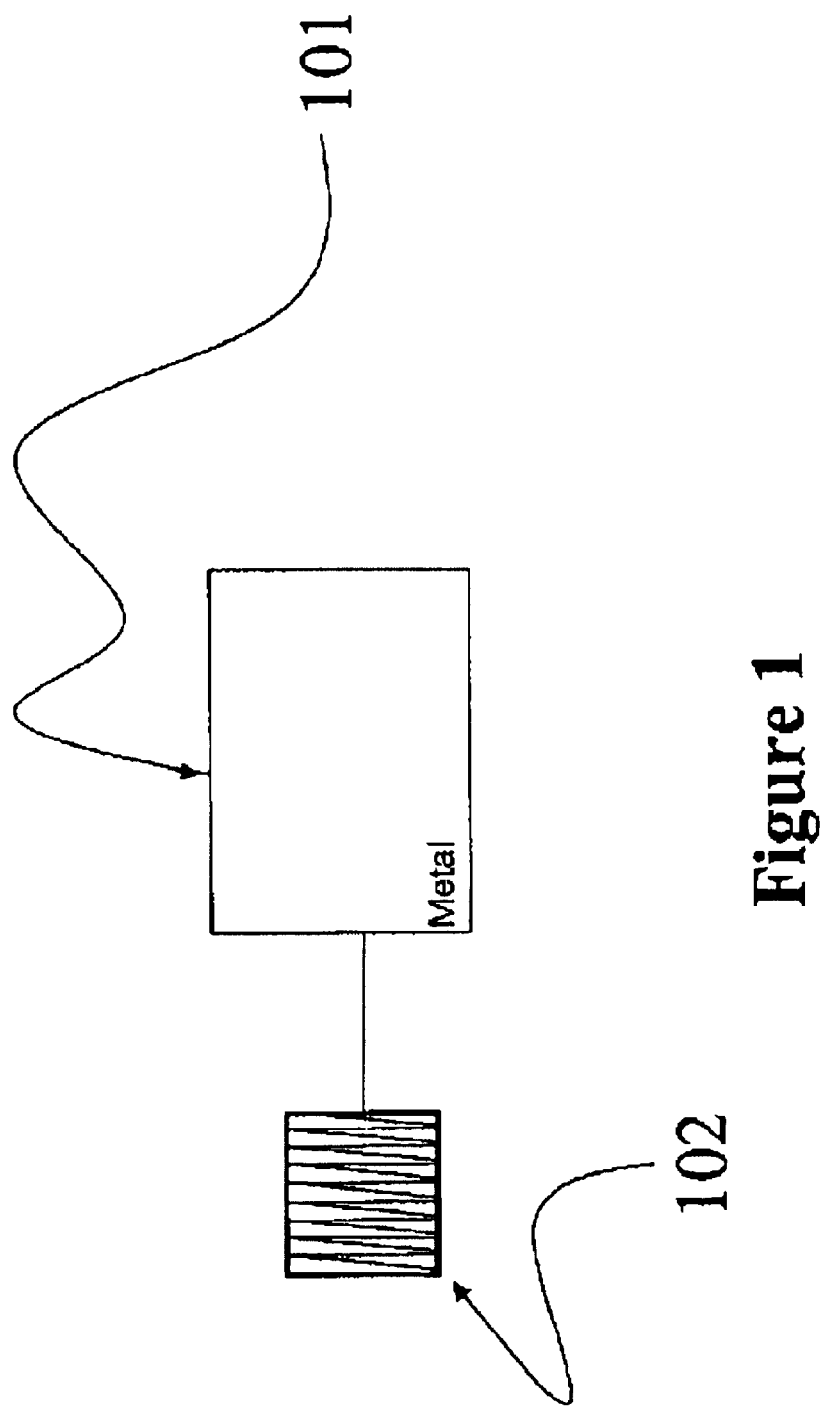
FIG. 1 is a representation of corrosion noise in unprotected metal.
Figure 2:
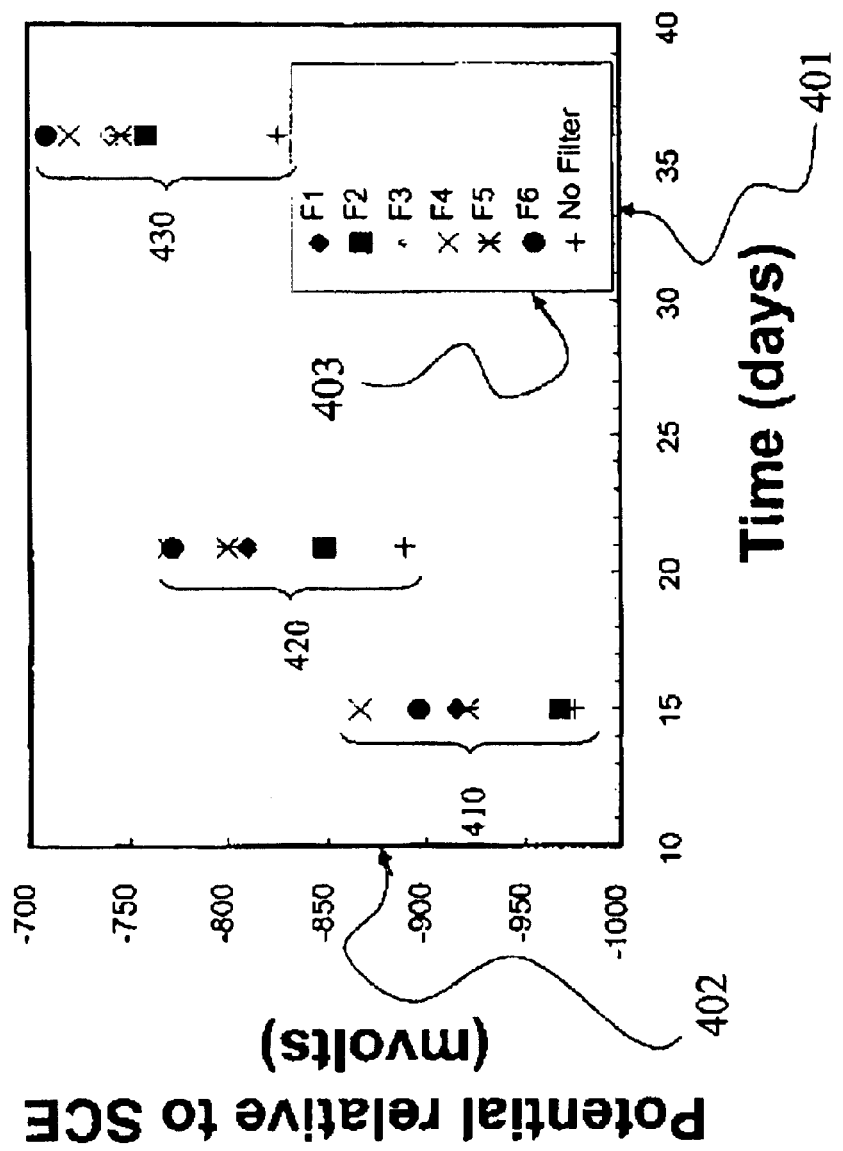
FIG. 2 is a graph of corrosion noise vs. time for various filters.
Figure 3:
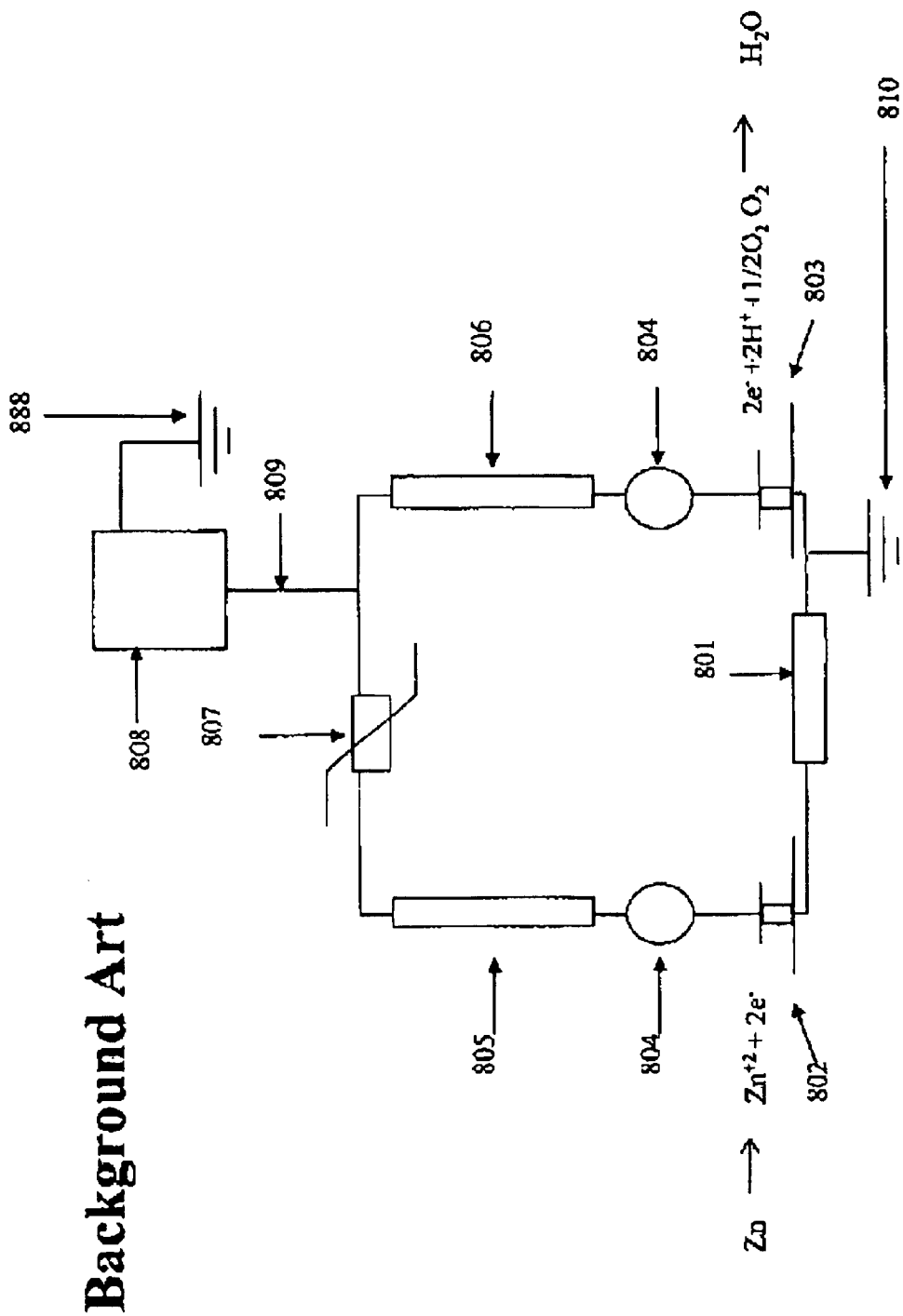
FIG. 3 is a circuit diagram of a corrosion noise reducing system without an Electronic Control Unit (ECU)

FIG. 3 shows an equivalent circuit diagram for the system of the Dowling patents and application. This figure abstracts the behavior of the system into a representative electrical circuit based on the electro-chemical nature of metal corrosion processes. Specifically, corrosion can be modeled as a fluctuating voltage source, the metal's inherent resistance can be represented, the anti-corrosion coating can be modeled as a varistor, and the noise filter can be modeled as a capacitor. By placing these modeled elements in a circuit diagram, the noise and filter components of Dowling can be more clearly conceptualized using electrical circuit analysis.

Within the representational circuit is a solution resistance 801 which represents the inherent resistance of the system in series with the galvanic electrode potential at the anode 802 which corresponds to the ionization process of zinc and the galvanic electrode potential at the cathode 803 which corresponds to the chemical process producing water. Also present and connected in series with the circuit are two noise sources 804, one of which is interposed between the galvanic electrode potential of the anode and the Faradaic impedance of the anode 805 and another interposed between the galvanic electrode potential at the cathode 803 and the Faradaic impedance of the cathode 806 placed in series between the Faradaic impedances of the anode and cathode are the zinc oxide varistor 807 and the noise filter 808. The varistor and noise filter act to reduce the occurrence of voltage fluctuations which can induce corrosion. The noise filter 808 may be active, passive, or both and, by selecting a node in the circuit to be designated common potential 810, the filter 808 can attenuate high frequencies in the circuit due to the corrosion noise.

Within the system of the present invention, rather than using a semiconductive coating, the present system relies on the use of one or more sacrificial anodes in a conventional cathodic protection system. Note, the one or more anodes would be sacrificial if operated as a cathodic protection system without the presence of the ECU. However, by connecting the ECU of the present system to either (or both) of the substrate (cathode) or the sacrificial anode, one can achieve not only the corrosion prevention of a cathodic protection system, but also one can prolong the lifetime of the anode. Within the present system, the filter properties of the ECU can be adjusted to minimize the sacrificial nature of the anode, or substantially eliminate the sacrifice of the anode, thus reducing maintenance and anode replacement costs, while providing corrosion protection for the substrate.

Figure 4:
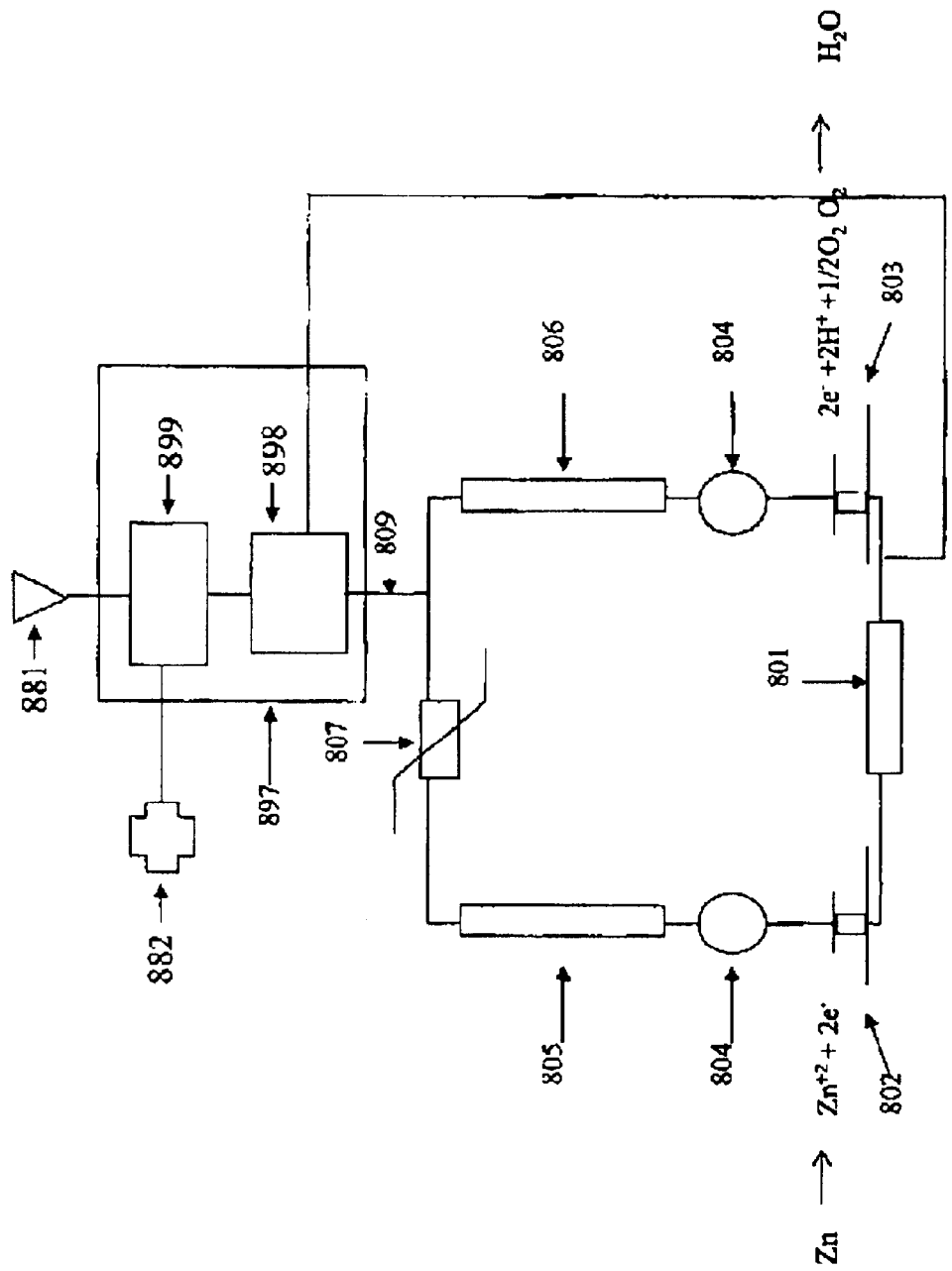
FIG. 4 is a circuit diagram of an ECU containing a controllable corrosion noise filter and ECU control circuit.

FIG. 4 is a circuit diagram of one embodiment of the present invention where components similar to those found in FIG. 3 retain their previous indicia. As shown, the ECU 897 contains a controllable filter 898 and an ECU control circuit 899. The ECU 897 may optionally be connected to one or more local sensors 882, and/or be connected to, and/or contain, an antenna (e.g., for use in wireless communication) 881 or other mechanism for achieving wireless communication, such as with optical transceivers. The ECU may also access data stored in a local data archive (not shown) or in a remote archive accessible via the antenna 881, other wireless communication mechanism or even wired connection, such as a network. The ECU control circuit 899 is configured to change a filter characteristic of the controllable filter 898, such that the frequency-dependent impedance of the controllable filter 898 is changed depending on the mode of the operation of the ECU control circuit 899. It is also to be appreciated that the present invention is not limited to this specific configuration, as will be appreciated by one of ordinary skill in the control system art.

Figure 5:
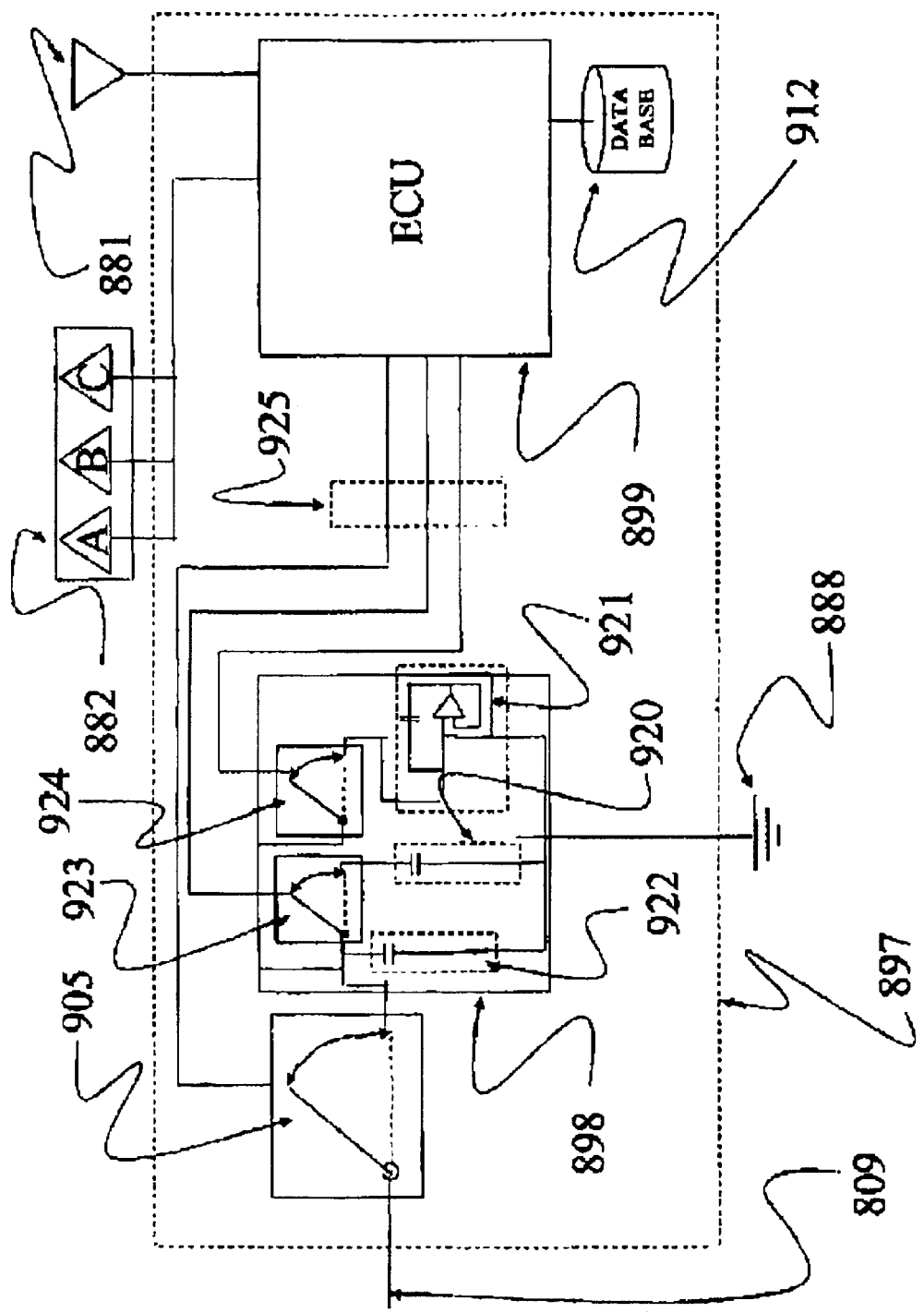
FIG. 5 is a block diagram of an ECU containing a controllable corrosion noise filter and ECU control circuit.

FIG. 5 is a block diagram of an embodiment of the present invention and includes an ECU 897 containing a controllable filter 898 and an ECU control circuit 899. While a filter composed of a single capacitor is shown, other circuit components may be used to implement various filters (e.g., having impedances in the form of notch filters) augmenting a low pass filter impedance characteristic. Schematically, the combination of the controllable filter 898 and an ECU control circuit 899 is represented as a single system 897 connected to the other elements of the corrosion system by a conductive link 809. The controllable filter 898 may include any configuration of various filters (e.g., filters having impedances in the form of low pass, notch filters, bandpass, etc.) configured to attenuate targeted high frequency signals corresponding to corrosion noise. The controllable filter 898 may optionally be disconnected from the system using an electronically controllable switch 905 that may be controlled by the ECU control circuit 899 or by other means such as a manual toggle switch, patch panel or other device that can automatically or manually, electrically insert and/or remove components from a circuit. The controllable filter 898 may be controlled by the ECU control circuit 899 by way of the control lines 925, which open or close switches 923 and 924 connecting a plurality of supplemental filters 920 and 921 (this may optionally include a switchable filter bank, which together can apply different filter characteristics to corrosion noise). It is also a feature of the invention that the ECU control circuit 899 electronically controls/adjusts the filter characteristics of the controllable filter 898 through adjustable circuit elements, which may optionally be voltage controlled resistors or switched variable capacitances. The ECU 950 may be connected to a wireless receiver/transmitter 881 so as to receive and/or transmit one or more control signals with a remote ECU control location (optionally thru a wireless electromagnetic and/or optical link). The ECU control circuit 899 may be connected to one or more local sensors 882, each configured to monitor one or more parameters used by the ECU control circuit 899 such as salinity, temperature, local position, or another parameter. Information received from the wireless receiver 881 and/or local sensors 882 may be used by the ECU control circuit 899 to adjust the controllable filter 898 or disconnect it entirely. Additionally, the ECU control circuit 899 may interface with a local and/or remote database 912 so as to process the information received from the wireless receiver/transmitter 881 and/or local sensors 882.

The increase in the lifetime can be optimized (maximized) through the use of filters with specific frequency response characteristics selected for the needs of a particular application, as well as the use of adaptive active filters, monitoring the "electrochemical noise" of the protected object and adjusting its response accordingly. Specific filters are configured and operated so as to excise corrosion noise thereby resulting in a smaller amplitude, low frequency voltage across the system. One or more filters are configured and attached to the substrate or anode in one or more places along the protected structure so as to provide a low resistance path to ground for 'high frequency' corrosion currents formed in and on the system. 'High frequency' is a term used herein to describe non-DC components of corrosion noise. In practice for typical structures, the high frequency component of corrosion noise is in the 10's of Hertz and higher. High frequency, as used herein, may also include the transition band between DC and 10 Hz for example, and thus includes frequencies at 1-10 Hz for example. Thus, cut off (or 3 dB points) of filter characteristics for controllable filters employed by the present invention are typically, although need not be limited to, 1 to 10 Hz. Depending on the nature of the corrosion noise, the filter characteristics may be adapted to suppress even lower frequencies, such as ¼, or ½ Hz and above, or even at one or more particular frequency bands (which may be notched out with one or more filters having impedances in the form of a notch filter).

Figure 6A:
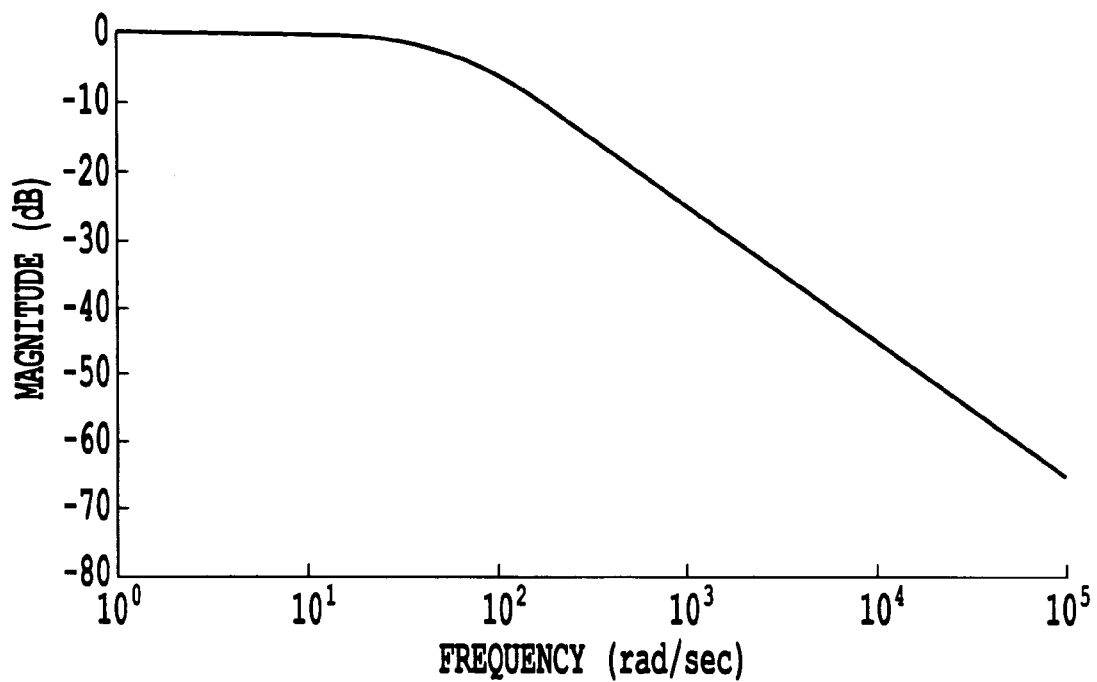
FIGS. 6A and 6B are amplitude and phase response curves, respectively, for a corrosion noise bandpass filter of one embodiment of the present invention.
Figure 6B:
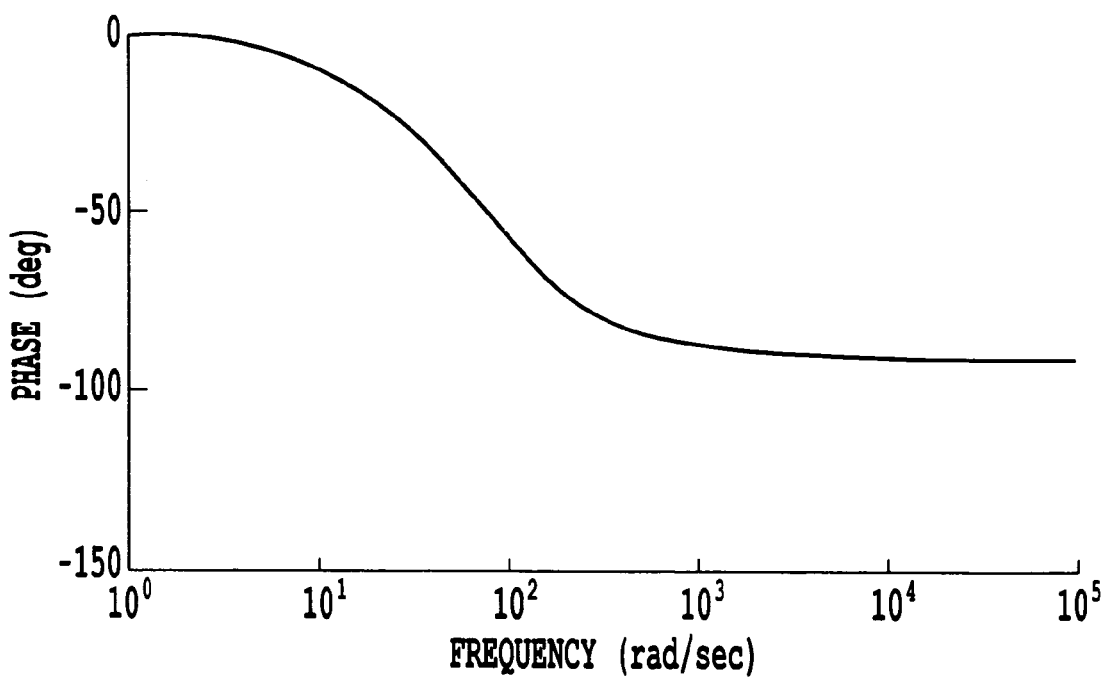

FIGS. 6A and 6B are amplitude and phase response curves, respectively, for impedance of an exemplary corrosion noise lowpass filter of one embodiment of the present invention. These Bode plots show a 3 dB point at about 10 Hz. Alternatively, filters having low pass impedance characteristic with 3 dB points of 5 Hz, 15 Hz, 25 Hz, 100 Hz or other values may be used depending on the protected material so long as significant non-DC components of spectral energy are removed from the protected structure so that voltage fluctuations outside the switch voltage range are significantly reduced. One or more of such filters having low pass impedance characteristic may be electrically connected to the protected structure at one or more locations to remove the unwanted corrosion noise energy while reducing or preventing any corrosion noise currents across the protected structure. One or more of these low pass filters may be controlled by the Electronic Control Unit in terms of filter frequency response and/or physical connection. Alternatively, higher-order filters may be used to change the roll-off rate of the characteristic curve, thereby further suppressing high frequency energy at frequencies closer to the 3 dB point. This electronic filter provides a path to ground for the electrochemical noise signal that induces loss of electrons and therefore corrosion. To effectively reduce corrosive effects, smaller impedances at lower frequencies need to be achieved (i.e., by increasing the size of the capacitor, if the system filter is purely a capacitor).

Figure 7A:
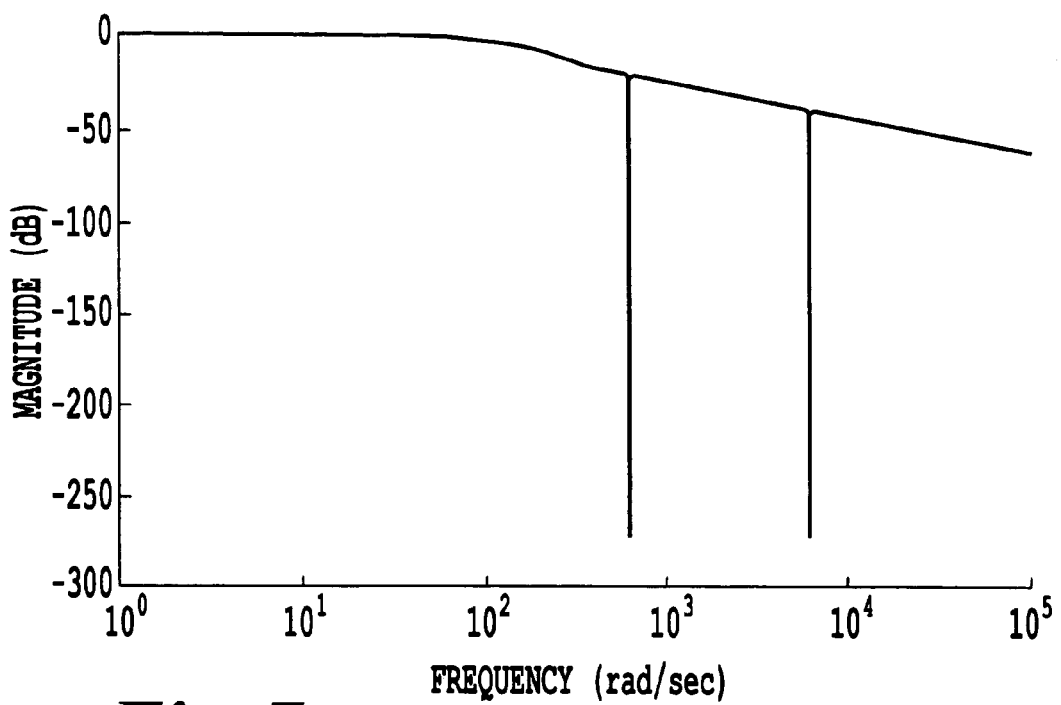
FIGS. 7A and 7B are amplitude and phase response curves, respectively, for a corrosion noise notch filter of one embodiment of the present invention.
Figure 7B:
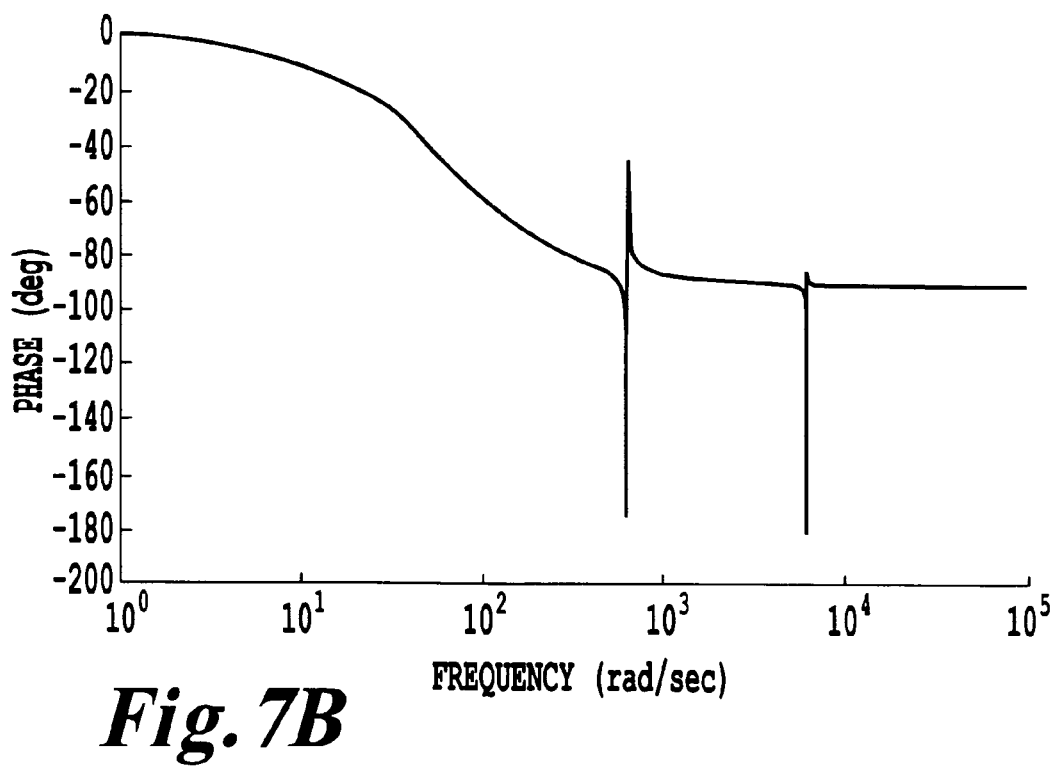

FIGS. 7A and 7B are amplitude and phase response curves, respectively, for a corrosion noise filter having low pass impedance characteristic augmented by notch filters of one embodiment of the present invention. As shown, multiple (or just one) notches in the impedance of the filter may be used in conjunction with the low pass impedance characteristic of FIGS. 6A and 6B to excise one or more corrosion noise spectral content. One or more such filters may be electrically connected to the protected structure at one or more locations to remove corrosion noise energy peaks while reducing or preventing any corrosion noise currents across the protected structure. One or more of these notch filters may be controlled by the Electronic Control Unit in terms of frequency response and/or physical connection. Alternatively, higher-order filters may be used.

The control of the one or more filters with low pass and/or notch impedance characteristics, and higher-order filter exercised by the Electronic Control Unit may be based on one or more corrosion noise measurements provided by one or more corrosion noise sensors monitoring the protected structure.

For all combinations of filters and filter connections, the effectiveness of the system can be further optimized over the life of the object being protected by configuring the ECU to adjust its filter operations in response to a series of measured and/or predetermined parameters to include one or more of: measured corrosion noise, temperature, salinity, humidity, location of vessel (e.g., North Sea vs. South China Sea), vessel moving or stationary, history of operation (e.g., ratio of time stationary vs. moving).

The control parameter measurement and exploitation aspects of the present invention are used to fine-tune the performance of the system for specific applications. Based on the control parameters, the requisite filter properties in the system can be determined and can be improved for consistent corrosion prevention over the entire surface of the structure, even in very large structures, such as aircraft carriers or large span bridges. In the present invention, the voltage fluctuations between the system and a low-noise high impedance reference electrode are monitored for when the voltage peak exceeds a predetermined threshold, a predetermined number of times, per time interval (e.g., 3-tens per second), and/or a heightened noise environment is detected. This threshold detection technique is one way to measure the standard deviation of the noise, which in turn is a measure of noise power. Alternatively, an FFT, or other signal processing technique, could be used to measure noise power as a function of frequency. The frequency content of the noise signal and its power content may be measured by such measuring devices such as a spectrum analyzer or through digitization of signal and performing various signal processing techniques in a real-time embedded processor in the ECU. In addition, other parameters may be used (individually or in combination) to manually or automatically adjust filter characteristics and/or filter duty (i.e., on/off) cycle. These include, but are not limited to, the previously identified parameters of: measured corrosion noise, temperature, salinity, humidity, location of vessel (e.g., North Sea vs. South China Sea), vessel moving or stationary, history of operation (e.g., ratio of time stationary vs. moving).

In another embodiment, the ECU is connected to a Global Positioning Satellite subsystem through an industry standard or proprietary bus such as VMEbus or through a wireless communication mechanism. By monitoring the geographic location of the system, the ECU adjusts the effective values of the corrosion noise filter characteristics according to predetermined criteria taking into account what is known about the effects of salinity, temperature, and other factors affecting corrosion that are associated with the system's geographic location.

Figure 8:
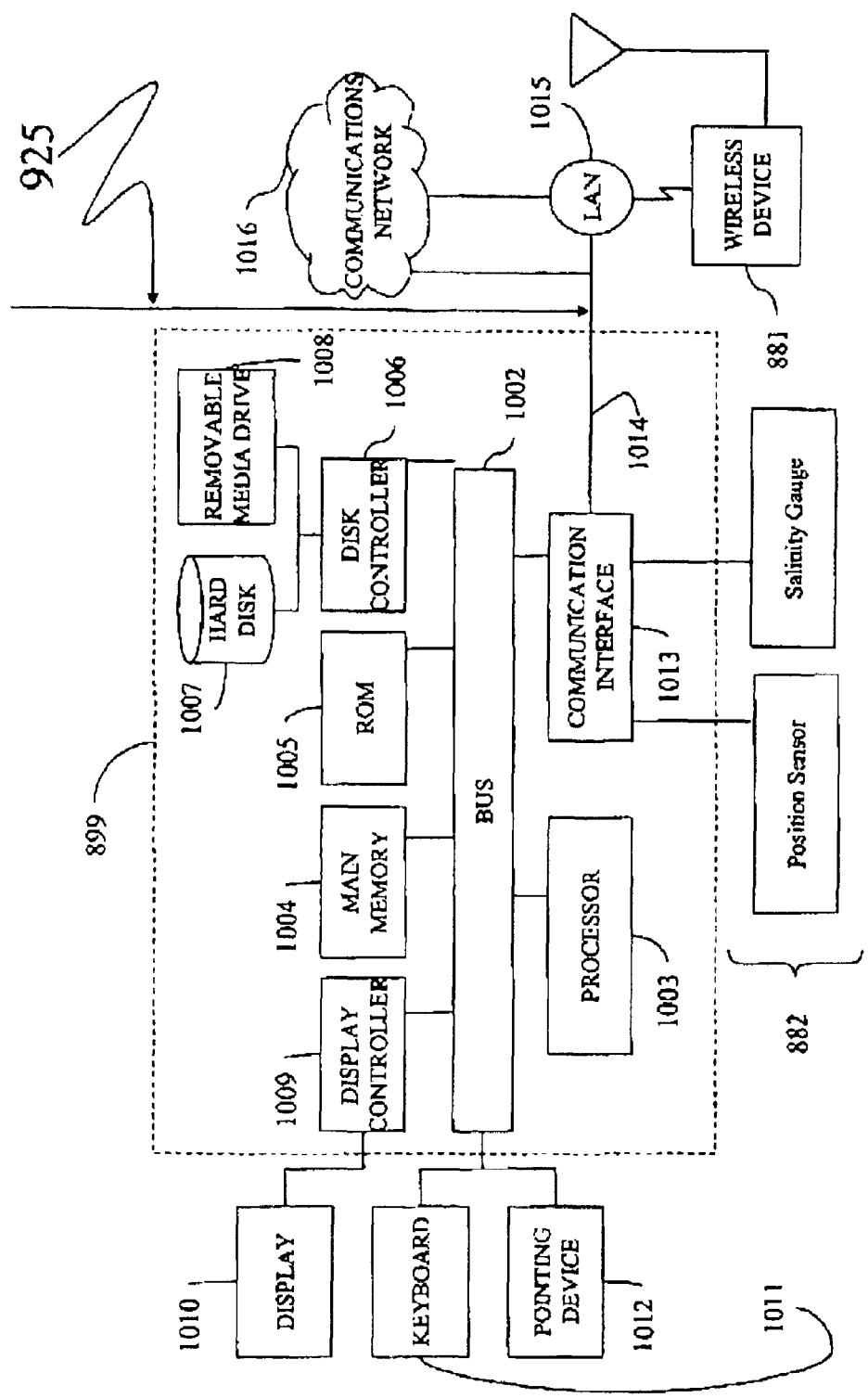
FIG. 8 is a block diagram of a computer system used in the present invention.

FIG. 8 shows a computer that can be used as an ECU control computer 899 in an embodiment of the present invention. The computer comprises a processor 1003, a main memory 1004, a ROM 1005, a system bus 1002, and is connected to various user interface devices 1010 through 1012 such as a monitor and keyboard. In order to monitor physical conditions and other variables relevant to optimizing the operation of the anti-corrosive and anti-fouling measures of the present invention, the computer is connected to sensors 882 such as salinity and pressure gauges, geographic position sensors, etc.

A more detailed description of the ECU control computer 899 follows. The ECU control computer 899 includes a bus 1002 or other communication mechanism for communicating information (possibly in a wireless manner), and a processor 1003 coupled with the bus 1002 for processing the information. The ECU control computer 899 also includes a main memory 1004, such as a random access memory (RAM) or other dynamic storage device (e.g., dynamic RAM (DRAM), static RAM (SRAM), and synchronous DRAM (SDRAM)), coupled to the bus 1002 for storing information and instructions to be executed by processor 1003. In addition, the main memory 1004 may be used for storing temporary variables or other intermediate information during the execution of instructions by the processor 1003. The ECU control computer 899 further includes a read only memory (ROM) 1005 or other static storage device (e.g., programmable ROM (PROM), erasable PROM (EPROM), and electrically erasable PROM (EEPROM)) coupled to the bus 1002 for storing static information and instructions for the processor 1003.

The ECU control computer 899 also includes a disk controller 1006 coupled to the bus 1002 to control one or more storage devices for storing information and instructions, such as a magnetic hard disk 1007, and a removable media drive 1008 (e.g., floppy disk drive, read-only compact disc drive, read/write compact disc drive, compact disc jukebox, tape drive, and removable magneto-optical drive). The storage devices may be added to the computer system 950 using an appropriate device interface (e.g., small computer system interface (SCSI), integrated device electronics (IDE), enhanced-IDE (E-IDE), direct memory access (DMA), or ultra-DMA).

The ECU control computer 899 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The ECU control computer 899 may also include a display controller 1009 coupled to the bus 1002 to control a display 1010, such as a cathode ray tube (CRT), for displaying information to a computer user. The computer system includes input devices, such as a keyboard 1011 and a pointing device 1012, for interacting with a computer user and providing information to the processor 1003. The pointing device 1012, for example, may be a mouse, a trackball, or a pointing stick for communicating direction information and command selections to the processor 1003 and for controlling cursor movement on the display 1010. In addition, a printer may provide printed listings of data stored and/or generated by the ECU control computer 899.

The ECU control computer 899 performs a portion or all of the processing steps of the invention in response to the processor 1003 executing one or more sequences of one or more instructions contained in a memory, such as the main memory 1004. Such instructions may be read into the main memory 1004 from another computer readable medium, such as a hard disk 1007 or a removable media drive 1008. One or more processors in a multi-processing arrangement may also be employed to execute the sequences of instructions contained in main memory 1004. In alternative embodiments, hard-wired circuitry may be used in place of or in combination with software instructions. Thus, embodiments are not limited to any specific combination of hardware circuitry and software.

As stated above, the ECU control computer 899 includes at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer can read.

Stored on any one or on a combination of computer readable media, the present invention includes software for controlling the ECU control computer 899, for driving a device or devices for implementing the invention, and for enabling the ECU control computer 899 to interact with a human user (e.g., print production personnel). Such software may include, but is not limited to, device drivers, operating systems, development tools, and applications software. Such computer readable media further includes the computer program product of the present invention for performing all or a portion (if processing is distributed) of the processing performed in implementing the invention.

The computer code devices of the present invention may be any interpretable or executable code mechanism, including but not limited to scripts, interpretable programs, dynamic link libraries (DLLs), Java classes, and complete executable programs. Moreover, parts of the processing of the present invention may be distributed for better performance, reliability, and/or cost.

The term "computer readable medium" as used herein refers to any medium that participates in providing instructions to the processor 1003 for execution. A computer readable medium may take many forms, including but not limited to, non-volatile media, volatile media, and transmission media. Non-volatile media includes, for example, optical, magnetic disks, and magneto-optical disks, such as the hard disk 1007 or the removable media drive 1008. Volatile media includes dynamic memory, such as the main memory 1004. Transmission media includes coaxial cables, copper wire and fiber optics, including the wires that make up the bus 1002. Transmission media also may also take the form of acoustic or light waves, such as those generated during radio wave and infrared data communications.

Various forms of computer readable media may be involved in carrying out one or more sequences of one or more instructions to processor 1003 for execution. For example, the instructions may initially be carried on a magnetic disk of a remote computer. The remote computer can load the instructions for implementing all or a portion of the present invention remotely into a dynamic memory and send the instructions over a telephone line using a modem. A modem local to the ECU control computer 899 may receive the data on the telephone line and use an infrared transmitter to convert the data to an infrared signal. An infrared detector coupled to the bus 1002 can receive the data carried in the infrared signal and place the data on the bus 1002. The bus 1002 carries the data to the main memory 1004, from which the processor 1003 retrieves and executes the instructions. The instructions received by the main memory 1004 may optionally be stored on storage device 1007 or 1008 either before or after execution by processor 1003.

The ECU control computer 899 also includes a communication interface 1013 coupled to the bus 1002. The communication interface 1013 provides a two-way data communication coupling to a network link 1014 that is connected to, for example, a local area network (LAN) 1015, or to another communications network 1016 such as the Internet. For example, the communication interface 1013 may be a network interface card to attach to any packet switched LAN. As another example, the communication interface 1013 may be an asymmetrical digital subscriber line (ADSL) card, an integrated services digital network (ISDN) card or a modem to provide a data communication connection to a corresponding type of communications line. Wireless links may also be implemented. In any such implementation, the communication interface 1013 sends and receives electrical, electromagnetic or optical signals that carry digital data streams representing various types of information.

The network link 1014 typically provides data communication through one or more networks to other data devices. For example, the network link 1014 may provide a connection to another computer through a local network 1015 (e.g., a LAN) or through equipment operated by a service provider, which provides communication services through a communications network 1016. The local network 1014 and the communications network 1016 use, for example, electrical, electromagnetic, or optical signals that carry digital data streams, and the associated physical layer (e.g., CAT 5 cable, coaxial cable, optical fiber, etc). The signals through the various networks and the signals on the network link 1014 and through the communication interface 1013, which carry the digital data to and from the ECU control computer 899 maybe implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The ECU control computer 899 can transmit and receive data, including program code, through the network(s) 1015 and 1016, the network link 1014 and the communication interface 1013. Moreover, the network link 1014 may provide a connection through a LAN 1015 to a mobile device 881 such as a personal digital assistant (PDA) laptop computer, or cellular telephone.

The present invention can be tailored for the prevention of corrosion of conductive materials that traditionally use cathodic protection. Suitable conductive material substrates include, but are not limited to: civilian and military aircraft; petroleum storage tanks; government, including roads and bridges, and Navy, Coast Guard and Army Corps of Engineers projects; chemical industry; pulp and paper industries; power plants; railroad bridges and rail cars; manufactured steel buildings, such as farm silos and warehouses; water towers; marine vessels; offshore platforms; and other marine structures. The ECU and cathodic protection system components can also be adapted for devices and/or vehicles associated with nuclear power plants, deep space missions, volcanic exploration and monitoring, and deep underwater exploration of toxic seismic environments.

Obviously, numerous modifications and variations of the present invention are possible in light of the above teachings. It is therefore to be understood that within the scope of the appended claims, the invention may be practiced otherwise than as specifically described herein.

What is claimed is:

1. A system for prolonging lifetime of one or more anodes of a cathodic corrosion protection system for controlling corrosion of a conductive structure in contact with a corrosive environment, comprising:
   one or more anode materials electrically connected to said conductive structure, wherein said one or more anode materials are electrically less noble than said conductive structure;
   a filter connected to at least one of said conductive structure, said one or more anodes, or a combination thereof, and having a controllable filter characteristic; and
   a electronic control apparatus connected to said filter, comprising a connection to at least one of a local sensor, a data base, and remote control device, and configured to control said controllable filter characteristic in correspondence with at least one of a locally sensed parameter, a stored parameter, and a remotely provided signal;
   wherein said conductive structure has no semiconductive coating thereon.

2. The system of claim 1, wherein said controllable filter characteristic is an impedance having the form of a low pass or notch filter.

3. The system of claim 1, wherein said filter comprises at least one:
   of an active filter;
   an adjustable passive filter; and
   a fixed passive filter.

4. The system of claim 3, wherein said filter is a plurality of passive filters and said controllable filter characteristic is controlled by switching from one of said plurality of passive filters to another of said plurality of passive filters.

5. The system of claim 3, wherein said filter is a single adjustable passive filter.

6. The system of claim 1, wherein said locally sensed parameter comprises at least one of:
   a corrosion noise parameter;
   a salinity parameter;
   a temperature parameter;
   a geographic position parameter;
   a time parameter;
   a solution purity parameter;
   a speed parameter;
   a depth parameter; and
   a pressure parameter.

7. The system of claim 1, wherein said stored parameter comprises at least one of:
   an object location history parameter;
   an anode duty cycle history parameter;
   an object location history parameter;
   a shape of said conductive structure parameter; and
   an object speed history parameter.

8. The system of claim 1, wherein said conductive structure comprises a metal selected from the group consisting of ferrous metals and conductive non-ferrous metals.

9. The system of claim 8, wherein said metal is steel.

10. The system of claim 8, wherein said metal is aluminum.

11. The system of claim 1, wherein said conductive structure is selected from the group consisting of marine vessels, marine structures, oil rigs, pipelines, power plants, and underwater structures.

12. The system of claim 1, wherein said one or more anodes comprises at least one material selected from the group consisting of conductive organic polymers, metals, metal alloys and non-metal semiconductor materials, wherein said at least one material is less noble than said conductive structure.

13. The system of claim 12, wherein said one or more anodes comprises at least one conductive organic polymer, wherein the conductive organic polymer is a member selected from the group consisting of polyacetylenes, polyphenylenes, polyfurans, polythiophenes, polypyrroles, poly(arylene vinylenes), polyanilines, and doped compositions thereof.

14. The system of claim 12, wherein said one or more anodes comprises at least one metal or metal alloy, wherein the metal or metal alloy comprises a metal selected from the group consisting of Zn, Ti, Al, Ga, Ce, Mg, Ba, Cs, the corresponding metal oxides and alloys thereof.

15. The system of claim 12, wherein said one or more anodes comprises at least one metal or metal alloy, wherein the metal or metal alloy comprises a mixture of one or more metals selected from the group consisting of Zn, Ti, Al, Ga, Ce, Mg, Ba and Cs and one or more metal oxides obtained therefrom.

16. The system of claim 15, wherein said one or more metals or metal alloys is a combination of zinc/zinc oxide.

17. An electronic control apparatus configured to control a corrosion noise reducing system including a controllable filter and one or more anodes electrically connected to a conductive structure, and said conductive structure having no semiconductive coating thereon, comprising:
   a first connection terminal configured to connect to said corrosion noise reducing system;
   a second connection terminal configured to connect to at least one of a local sensor, a data base, and remote control device; and
   a control mechanism configured to control said controllable filter via a control signal sent over said first connection terminal in correspondence with at least one of a locally sensed parameter, a stored parameter, and a remotely provided signal.

18. The apparatus of claim 17, wherein said controllable filter has a controllable filter characteristic which is an impedance having the form of a low pass or notch filter.

19. The apparatus of claim 17, wherein said controllable filter is a plurality of passive filters having impedances that differ one from the other and said controllable filter characteristic is controlled by switching from one of said plurality of passive filters to another of said plurality of passive filters.

20. The apparatus of claim 17, wherein said controllable filter is a single adjustable passive filter.

21. The apparatus of claim 17, wherein said locally sensed parameter comprises at least one of:
   a corrosion noise parameter;
   a salinity parameter;
   a temperature parameter;
   a geographic position parameter;
   a time parameter;
   a solution purity parameter;
   a speed parameter;
   a depth parameter; and
   a pressure parameter.

22. The apparatus of claim 17, wherein said stored parameter comprises at least one of:
   an object location history parameter,
   an anode duty cycle history parameter,
   an object location history parameter,
   a shape of conductive structure parameter, and
   an object speed history parameter.

23. The apparatus of claim 17, wherein said conductive structure comprises a metal selected from the group consisting of ferrous metals and conductive non-ferrous metals.

24. The apparatus of claim 23, wherein said metal is steel.

25. The apparatus of claim 23, wherein said metal is aluminum.

26. The apparatus of claim 17, wherein said conductive structure is selected from the group consisting of marine vessels, marine structures, oil rigs, pipelines, power plants, and underwater structures.

27. The apparatus of claim 17, wherein said one or more anodes comprises at least one material selected from the group consisting of conductive organic polymers, metals, metal alloys and non-metal semiconductor materials, wherein said at least one material is less noble than said conductive structure.

28. The apparatus of claim 27, wherein said one or more anodes comprises at least one conductive organic polymer, wherein the conductive organic polymer is a member selected from the group consisting of polyacetylenes, polyphenylenes, polyfurans, polythiophenes, polypyrroles, poly(arylene vinylenes), polyanilines, and doped compositions thereof.

29. The apparatus of claim 27, wherein said one or more anodes comprises at least one metal or metal alloy, wherein the metal or metal alloy comprises a metal selected from the group consisting of Zn, Ti, Al, Ga, Ce, Mg, Ba, Cs, the corresponding metal oxides and alloys thereof.

30. The apparatus of claim 27, wherein said one or more anodes comprises at least one metal or metal alloy, wherein the metal or metal alloy comprises a mixture of one or more metals selected from the group consisting of Zn, Ti, Al, Ga, Ce, Mg, Ba and Cs and one or more metal oxides obtained therefrom.

31. The apparatus of claim 30, wherein said one or more metals or metal alloys is a combination of zinc/zinc oxide.

32. A method for prolonging lifetime of one or more anodes of a cathodic protection system for preventing corrosion of a conductive structure in contact with a corrosive environment, said method comprising:
   connecting, to said conductive structure, one or more anodes that are less noble than said conductive structure;
   connecting an electronic control unit to a controllable filter that is connected to at least one of said one or more anodes, said conductive structure, or both;
   filtering corrosive noise in the conductive structure or one or more anodes with said controllable filter;
   monitoring at least one parameter associated with a corrosion of said one or more anodes; and
   adjusting a filter characteristic of said controllable filter in correspondence with said at least one parameter;
   wherein said conductive structure has no semiconductive coating thereon.

33. The method of claim 32, wherein said filter characteristic is an impedance having the form of a low pass or notch filter.

34. The method of claim 32, wherein said controllable filter is a plurality of passive filters differing one from the other in at least said filter characteristic and said filter characteristic is controlled by switching from one of said plurality of passive filters to another of said plurality of passive filters.

35. The method of claim 32, wherein said controllable filter is a single adjustable passive filter.

36. The method of claim 32, wherein said at least one parameter comprises:
   a corrosion noise parameter;
   a salinity parameter;
   a temperature parameter;
   a geographic position parameter;
   a time parameter;
   a solution purity parameter;
   a speed parameter;
   a depth parameter;
   a pressure parameter;
   an object location history parameter;
   an anode duty cycle history parameter;
   an object location history parameter;
   a shape of conductive structure parameter; and
   an object speed history parameter.

37. The method of claim 32, wherein said conductive structure comprises a metal selected from the group consisting of ferrous metals and conductive non-ferrous metals.

38. The method of claim 37, wherein said metal is steel.

39. The method of claim 37, wherein said metal is aluminum.

40. The method of claim 32, wherein said conductive structure is selected from the group consisting of marine vessels, marine structures, oil rigs, pipelines, power plants, and underwater structures.

41. The method of claim 32, wherein said one or more anodes comprises at least one material selected from the group consisting of conductive organic polymers, metals, metal alloys and non-metal semiconductor materials, wherein said at least one material is less noble than said conductive structure.

42. The method of claim 41, wherein said one or more anodes comprises at least one conductive organic polymer, wherein the conductive organic polymer is a member selected from the group consisting of polyacetylenes, polyphenylenes, polyfurans, polythiophenes, polypyrroles, poly(arylene vinylenes), polyanilines, and doped compositions thereof.

43. The method of claim 41, wherein said one or more anodes comprises at least one metal or metal alloy, wherein the metal or metal alloy comprises a metal selected from the group consisting of Zn, Ti, Al, Ga, Ce, Mg, Ba, Cs, the corresponding metal oxides and alloys thereof.

44. The method of claim 41, wherein said one or more anodes comprises at least one metal or metal alloy, wherein the metal or metal alloy comprises a mixture of one or more metals selected from the group consisting of Zn, Ti, Al, Ga, Ce, Mg, Ba and Cs and one or more metal oxides obtained therefrom.

45. The method of claim 44, wherein said at least one metal or metal alloy is a combination of zinc/zinc oxide.

46. A system for prolonging lifetime of one or more anodes in a cathodic protection system for preventing corrosion of a conductive structure in contact with a corrosive environment, said conductive structure electrically connected to one or more anodes that are less noble that said conductive structure, said system comprising:

means for filtering corrosive noise from either or both of said conductive structure or said one or more anodes;

means for monitoring at least one parameter associated with the corrosion of said conductive structure or said one or more anodes; and means for adjusting said electronic filter in correspondence with said at least one parameter;

wherein said conductive structure has no semiconductive coating thereon.

47. The system of claim 46, wherein said means for monitoring includes a computer program product.

* * * * *